United States Patent [19]

Johnson, IV et al.

[11] Patent Number: 4,803,978
[45] Date of Patent: Feb. 14, 1989

[54] APPARATUS FOR ACTUATING AN INHALER

[76] Inventors: John J. Johnson, IV, 80 Calle San Blas, Albuquerque, N. Mex. 87109; John J. Johnson, Jr., 720 University Ave., Las Vegas, N. Mex. 87701

[21] Appl. No.: 88,994

[22] Filed: Aug. 21, 1987

Related U.S. Application Data

[63] Continuation of Ser. No. 764,189, Aug. 9, 1985, abandoned.

[51] Int. Cl.$^4$ ............................................. A61M 15/00
[52] U.S. Cl. ........................... 128/200.23; 128/203.15; 128/204.26
[58] Field of Search ...................... 128/200.23, 203.15, 128/204.26–204.29, 205.15, 14 205.16, 205.24, 203.23; 222/402.13, 61

[56] References Cited

U.S. PATENT DOCUMENTS

| | | | |
|---|---|---|---|
| 3,107,670 | 10/1963 | Silson et al. | 128/200.23 |
| 3,157,179 | 11/1964 | Paullus et al. | 128/200.23 |
| 3,187,748 | 6/1965 | Mitchell et al. | 128/200.23 |
| 3,356,088 | 12/1967 | Nelson | 128/200.23 |
| 3,456,646 | 7/1969 | Phillips et al. | 128/200.23 |
| 3,636,949 | 1/1972 | Kropp | 128/200.23 |
| 3,789,843 | 2/1974 | Armstrong et al. | 128/200.23 |
| 3,814,297 | 6/1974 | Warren | 128/200.23 X |
| 3,826,413 | 7/1974 | Warren | 128/200.23 X |
| 4,414,972 | 11/1983 | Young et al. | 128/200.23 |
| 4,576,157 | 3/1986 | Raghuprasad | 128/200.23 |

Primary Examiner—Kyle L. Howell
Assistant Examiner—Angela D. Sykes
Attorney, Agent, or Firm—Cahill, Sutton & Thomas

[57] ABSTRACT

Apparatus, having an outlet port insertable within a user's mouth, has housed therein an automatically actuated commercially available and replaceable inhaler for discharging a medicated vapor through the outlet port into the user's mouth upon inhalation. A pivotable spring loaded plate within the apparatus bears upon the inhaler to actuate the inhaler upon operation of a trigger mechanism. The trigger mechanism includes a valve operable in response to a slight vacuum developed within the apparatus upon inhalation by a user. Operation of the valve anularly displaces a sear to release a cam associated with a pivot mechanism of the spring loaded plate. The released cam permits rotation of the spring loaded plate to effect discharge from the inhaler into the user's mouth. A manually operated rocker arm recocks the spring loaded plate and rotates the cam into engagement with the sear to retain the spring loaded plate in the cocked state.

19 Claims, 1 Drawing Sheet

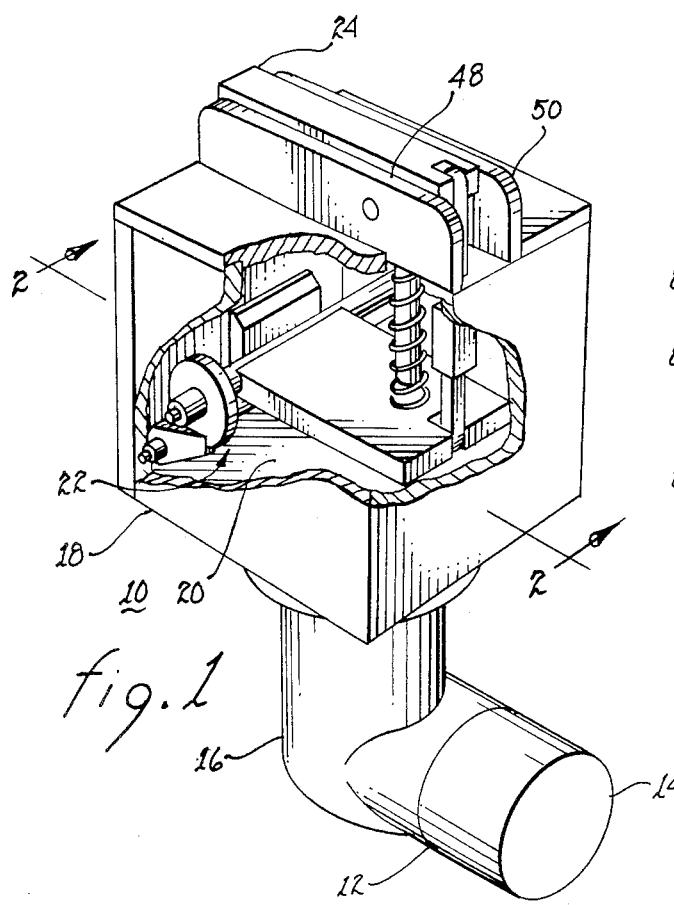
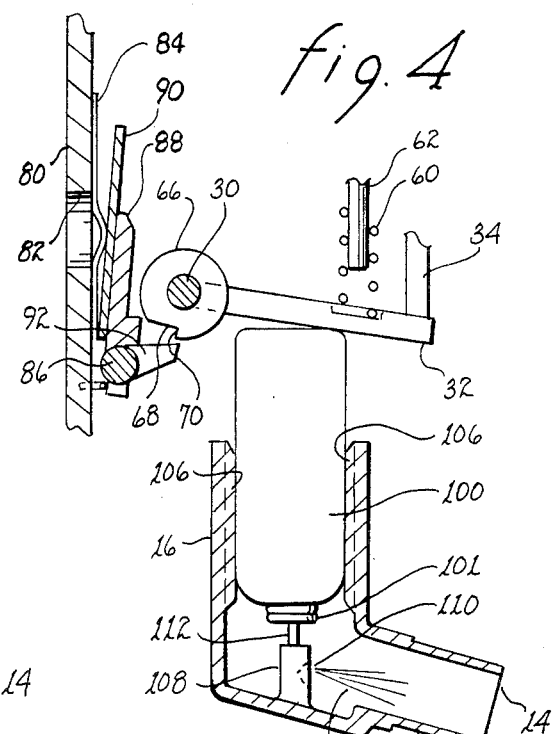
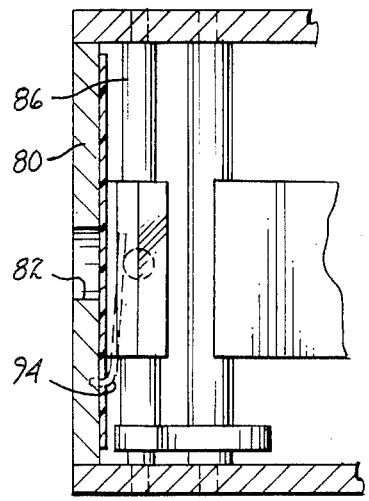
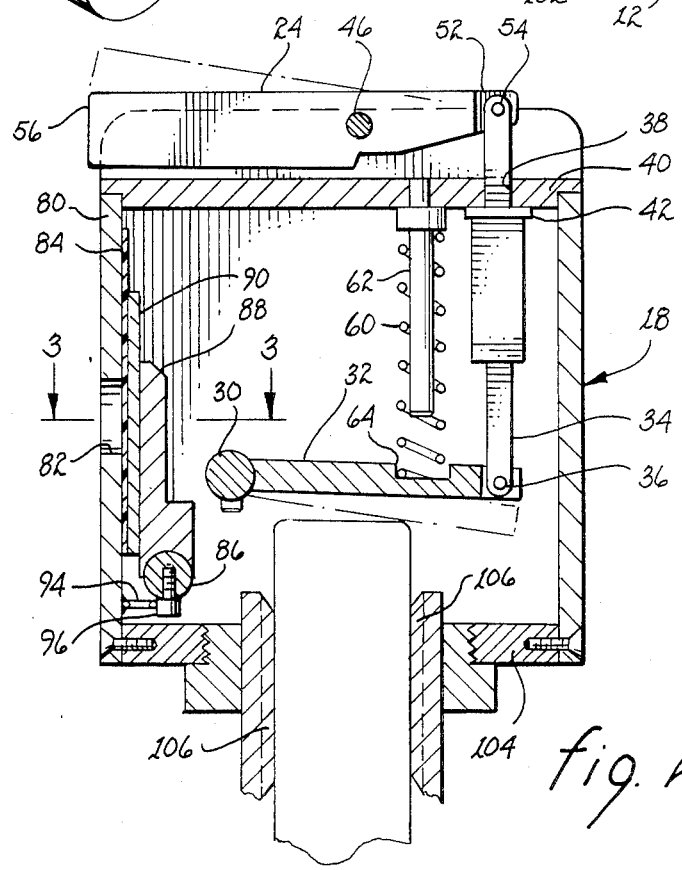

APPARATUS FOR ACTUATING AN INHALER

This application is a continuation of U.S. patent application Ser. No. 764189, filed Aug. 9, 1985, now abandoned.

FIELD OF THE INVENTION

The present invention relates to respiratory devices and, more particularly, apparatus responsive to inhalation for actuating commercially available inhalers capable of discharging a medicated vapor spray.

DESCRIPTION OF RELATED ART

Many persons suffering from emphysema and other respiratory diseases or disabilities have difficulty breathing from time to time, depending upon the activity engaged, degree of inflamation of respiratory tissues and other stresses. A number of medications are usable to alleviate the debilitating symptoms or restore normal breathing. Many of these medications are dispensed from aerosol-like dispensers as a vapor to be inhaled directly into the lungs. The dispenser may include an outlet port to be placed in the user's mouth in sealed relationship to ensure passage of the medication down the user's throat and into his lungs. Actuation of these devices generally requires a compressive force to be exerted by a user's hand after the outlet port is placed within the mouth.

For many persons, actuation of the device is of no moment. However, many persons having a need for such inhalers may also suffer from the debilitating effects and limitations attendant arthritic hands. Some of these persons no longer have the requisite strength or manual dexterity to compress the inhalers. Yet other persons may become too disoriented or otherwise not be capable of using the inhalers when needed which debility may be caused in part by the difficulty experienced in breathing.

In an effort to overcome the need to compress an inhaler in order to use it, numerous devices have been developed as attachments to such inhalers. Some of these devices require actuation of a mechanical element which directly or indirectly compresses the inhaler to provide discharge of the medicated vapor. Such devices are not readily usable by persons who are not fully dexterous or persons who may become disoriented due to or as a result of breathing difficulties. Yet other devices have a triggering mechanism which is manually actuated. Upon actuation, the medicated vapor is discharged from the inhaler. Again, such devices require a degree of dexterity which may not be available to every actual or potential user due to physical fraility or disorientation.

The following U.S. Patents disclose prior art devices of the type described above: U.S. Pat. Nos. 3,157,179, 3,187,748, 3,356,088, 3,456,644, 3,456,646, 3,656,070, 3,636,949, 3,789,843, 3,814,297, 3,826,413.

SUMMARY OF THE INVENTION

The present invention includes a sealed container having replaceably located therein a commercially available inhaler and an outlet port in fluid communication with the inhaler to discharge automatically a medicated vapor directly into the user's lungs. A valve, responsive to a below atmospheric pressure within the apparatus, angularly displaces a sear in locking engagement with a cam. The cam is pivotally supported and includes a spring loaded plate extending therefrom for compressing the inhaler in response to extension of the spring. A cocking mechanism compresses the spring and retains the plate in a cocked state pending operation of the triggering mechanism initiated by operation of the valve. In operation, a user places the outlet port within his mouth and begins to inhale. The resulting pressure drop within the apparatus actuates the valve of the trigger mechanism to release and uncock the spring loaded plate. The plate, in response to the spring, compresses the inhaler to cause a discharge of the medicated vapor spray through the outlet port directly into the mouth, throat and lungs of the user.

It is therefore a primary object of the present invention to provide a device for actuating an inhaler in response to inhalation by a user.

Another object of the present invention is to provide a device which requires only that the outlet port thereof be placed within the user's mouth to obtain a discharge of medicated vapor upon inhalation.

Yet another object of the present invention is to provide a device for automatically discharging a medicated vapor at the moment of need.

Still another object of the present invention is to provide a vacuum responsive triggering mechanism for actuating an inhaler.

A still further object of the present invention is to provide a method for discharging a medicated vapor into the lungs of a user in response to inhalation by the user.

A yet further object of the present invention is to provide a method for actuating an inhaler in response to inhalation by a user.

These and other objects of the present invention will become apparent to those skilled in the art as the description there proceeds.

BRIEF DESCRIPTION OF THE DRAWINGS

The present invention will be described with greater specificity and clarity with reference to the following drawings, in which:

FIG. 1 is a partially cut away isometric view of the present invention;

FIG. 2 is a cross-sectional view taken along lines 2—2, as shown in FIG. 1;

FIG. 3 is a partial cross-sectional view taken along lines 3—3, as shown in FIG. 2; and FIG. 4 is a cross-sectional view illustrating the operative elements in the uncocked state.

DESCRIPTION OF THE PREFERRED EMBODIMENT

Referring to FIG. 1, there is shown an apparatus 10 having a conduit 12 terminating at an outlet port 14. The conduit and outlet port are sized to permit placement within a user's mouth and without meaningful restriction of a medicated vapor discharged therethrough. A cylindrical housing 16 supports therein an inhaler in fluid communication with outlet port 14. An enclosure 18, supported upon housing 16, defines a chamber 20 within which a triggering mechanism, generally referenced by numeral 22, is housed. A rocker arm 24 is pivotally located upon enclosure 18 for cocking the actuating mechanism attendant the inhaler.

Referring primarily to FIG. 2, details of the actuating and triggering mechanisms will be described. A shaft 30 is pivotally mounted in opposed sides of enclosure 18. Plate 32 is rigidly attached to the shaft and is angularly displaced commensurate with rotation of the shaft. A rod 34 is pivotally attached to the free end of plate 32 through a pivot mechanism 36. The rod extends upwardly into penetrable engagement with an aperture 38 located in top 40 of enclosure 18. An annular flange 42 or the like is disposed upon rod 34 to form a seal about aperture 38 when plate 32 is in the cocked position. Rocker arm 24 is pivotally secured at pivot 46 intermmediate protective flanges 48, 50 extending upwardly from top 40. End 52 of the rocker arm is pivotally secured to the upper end of rod 34 through pivot mechanism 54. On inspection, it will be noted that on exerting a downward force upon end 56 of the rocker arm, upward rectilinear translation of rod 34 will occur which in turn will angularly displace upwardly plate 32 to the cocked position. Preferably, the upper surface of the rocker arm will be essentially coincident with the upper edges of adjacent flanges 48, 50 when plate 32 is in the cocked position.

An ongoing downward force is exerted upon plate 32 by coil spring 60 secured to and extending downwardly from alignment post 62, the latter depending from top 40. A depression 64 is formed in plate 32 to receive and retain the lower end of the coil spring and maintain it in alignment with the post. As depicted in FIGS. 1, 3 and 4, a cam 66 is mounted upon shaft 30. The cam is essentially circular and includes an indentation 68 which indentation incorporates a shoulder 70.

Referring jointly to FIGS. 2, 3 and 4, triggering mechanism 22 will be described in detail. Side wall 80 includes an aperture 82. A flexible membrane 84 is secured adjacent the inner surface of side wall 80 in circumscribing relationship to aperture 82. A shaft 86 is pivotally secured to opposing walls of enclosure 18. An arm 88 is secured to and extends upwardly from shaft 86 for supporting a plate 90. The location and size of plate 90 is selected to overlap the outline of aperture 82 in side wall 80; moreover, in one rotational state of shaft 86, plate 90 is adjacent and parallel to flexible membrane 84.

A sear 92 extends from shaft 86 in general alignment with cam 66 for engaging indentation 68 and bearing against shoulder 70 when plate 32 is in the cocked state. A leaf spring 94 extends from side wall 80 and bears against a bolt 96 or similar protrusion extending downwardly from shaft 86. The force exerted by leaf spring 94 upon shaft 86 will tend to bias plate 90 adjacent membrane 84. As illustrated in FIG. 1, when plate 32 is in the cocked position, shaft 86 is angularly displaced by force of leaf spring 94 to engage sear 92 with indentation 68 in cam 66. The resulting interference between the sear and shoulder 70 will preclude rotation of shaft 30 and commensurate downward angular displacement of plate 32; the plate will be retained in the cocked state by the sear.

Angular rotation of shaft 86 (in the clockwise direction as illustrated in FIG. 4) will withdraw sear 92 from engagement with shoulder 70. Such disengagement will remove the rotational restraint imposed upon plate 32 and the plate will rotate downwardly in response to the force exerted by coil spring 60. Thereafter, sear 92 may rest on the peripheral surface of cam 66. On cocking of plate 32 by exerting a downward force upon rocker arm 24, cam 66 will rotate to permit engagement of the sear with indentation 68. Because of the rotational force exerted by leaf spring 94 upon shaft 86, the sear will be biased counterclockwise into the indentation.

Referring primarily to FIGS. 1, 2 and 4, the mounting of inhaler 100 and the discharge of medicated vapor 102 will be described. Housing 16 is removably attachable to base 104 of enclosure 18 to permit replacement of inhaler 100 within the housing. The inhaler is supported by and vertically slidable with respect to ribs 106 extending inwardly within the housing in response to a force exerted by plate 32. Within neck 112 of inhaler 100 there is located a valve for releasing flow of medicated vapor from within the inhaler through nozzle 110 in response to relative compressive displacement between the neck and the nozzle. The neck also includes bias means for extending the nozzle away from the neck on cessation of the compressive force. A boss 108 is formed within conduit 12 to support and bear against nozzle 110 extending from inhaler 100. The boss includes a passageway for receiving discharge of medicated vapor from nozzle 110 and for directing the discharge laterally through an aperture 110 into conduit 12. It may therefore be appreciated that downward displacement of the body of inhaler 100 will result in compressive displacement between neck 112 and nozzle 110 to activate the valve within the neck and permit flow of medicated vapor from the nozzle. The discharged medicated vapor is thereafter conveyed via boss 108 and conduit 12 through outlet port 14.

In operation, a user cocks spring loaded plate 32 by depressing end 56 of rocker arm 24. The resulting upward movement of the plate will permit the body of inhaler 100 to be displaced upwardly within housing 16 in response to the bias force within neck 112 of the inhaler. To use the device, conduit 12 is placed into one's mouth and the user begins to inhale. The resulting below atmospheric pressure within conduit 12 is translated through the spaces defined by ribs 106 and the inhaler within into chamber 20 of enclosure 18. The resulting difference in pressure between atmospheric pressure and that within chamber 20 will cause flexible membrane 84 in proximity to aperture 82 to flex inwardly. The inward flexure of the membrane, as depicted in FIG. 4, will force plate 90 to rotate clockwise about shaft 86. The resulting commensurate rotation of shaft 86 will disengage sear 92 from indentation 68 in cam 66. Such disengagement permits rotation of the cam and downward angular movement of spring loaded plate 32, which movement will occur in response to the force exerted by coil spring 60. The downward movement of the plate, acting upon the body of inhaler 100, will result in downward movement of the inhaler with respect to the positionally maintained nozzle 110. The resulting relative displacement between the inhaler and the nozzle will open the valve located within neck 112 and a measured charge of medicated spray will flow through the nozzle into boss 108 and out through aperture 110 into conduit 12 and through outlet port 14.

To reset apparatus 10, end 56 of rocker arm 24 is depressed to a location essentially coincident with that of the upper edges of flanges 48, 50. The resulting release of force upon inhaler 100 will permit the inhaler to rise relative to nozzle 110 in response to the bias force located within neck 112. Additionally, the now existing lack of differential between atmospheric pressure and the pressure within chamber 18 will permit membrane 84 to be essentially planar to side wall 80. In response to the force exerted by leaf spring 94, shaft 86 will rotate counterclockwise to locate plate 90 adjacent membrane 84 and sear 92 into locking engagement with indentation 68 of cam 66. The device is now cocked for discharging a further quantity of medicated vapor.

As will become apparent, actuation of apparatus 10 does not require any manual dexterity. Instead, the user need only place conduit 12 within his mouth and begin to inhale. This capability is particularly important for those actual and potential users who are physically disabled due to disease or accident and for those who tend to be or may become disoriented at the time medication is needed.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

We claim:

1. Apparatus usable with an inhaler having a body, a nozzle and a valve responsive to relative displacement between the body and the nozzle for discharging the charge of medicated vapor for actuating the inhaler to discharge a charge of medicated vapor from the inhaler directly into the oral cavity of a user upon inhalation by the user, said apparatus comprising in combination:
   (a) an enclosure;
   (b) a housing means associated with said enclosure for retaining the nozzle of the inhaler in a fixed location and for slidably supporting the body of the inhaler;
   (c) an actuating means disposed in said enclosure for actuating the valve of the inhaler to eject a charge of the medicated vapor by slidably repositioning the body of the inhaler toward the nozzle of the inhaler;
   (d) a triggering means disposed in said enclosure for triggering operation of said actuating means;
   (e) a conduit in fluid communication with said enclosure and having an outlet port insertable within the user's mouth for channelling the charge of medicated vapor through the outlet port;
   (f) said triggering means including a trigger valve disposed within said enclosure for initiating operation of said triggering means to trigger said actuating means, said trigger valve being responsive to a pressure drop within said enclosure;
   (g) means mechanically attached to said actuating means and extending from said enclosure for cocking said actuating means upon cessation of the pressure drop within the enclosure, said cocking means being operable while said outlet is within the user's mouth; and
   (h) means for essentially precluding a flow of air into said enclosure before, during, and after operation of said triggering means;
   whereby, on placement of said outlet port within the user's mouth and upon inhalation by the user, a pressure drop within said enclosure occurs to trigger said actuating means and bring about a discharge and channelling of medicated vapor from the inhaler into the user's oral cavity and lungs.

2. The apparatus as set forth in claim 1 wherein said triggering means includes means for uncocking said actuating means.

3. The apparatus as set forth in claim 2 wherein said uncocking means includes a sear.

4. The apparatus as set forth in claim 3 wherein said uncocking means includes a cam cooperating with said sear.

5. The apparatus as set forth in claim 1 including means for urging said actuating means toward the inhaler.

6. The apparatus as set forth in claim 5 including means for biasing said triggering means.

7. The apparatus as set forth in claim 1 including means for replacing the inhaler.

8. The apparatus as set forth in claim 7 wherein said replacing means includes means for disengaging said retaining means from said enclosure.

9. The apparatus as set forth in claim 1 wherein said retaining means includes means for supporting the inhaler and means for channelling air past the inhaler and through said retaining means to permit limited air flow between said enclosure and said outlet port.

10. The apparatus as set forth in claim 1 wherein said actuating means includes a plate for contacting the inhaler, means for pivoting said plate and means for biasing said plate against the inhaler and about said pivoting means.

11. The apparatus as set forth in claim 1 wherein said pressure responsive means comprises an aperture in a wall of said enclosure, a diaphragm juxtaposed to the inside surface of said wall, said diaphragm being flexibly responsive to a difference in air pressure between the air adjacent said aperture and the air within said enclosure and means for sensing flexing of said diaphragm into said enclosure in response to such a pressure differential.

12. The apparatus as set forth in claim 11 wherein said actuating means includes biasing means for maintaining said actuating means in a cocked state and for actuating the inhaler upon uncocking of said actuating means.

13. The apparatus as set forth in claim 12 wherein said triggering means includes a sear responsive to said sensing means for uncocking said actuating means.

14. The apparatus as set forth in claim 13 wherein said actuating means includes a cam positionally maintained by said sear prior to flexing of said diaphragm.

15. The apparatus as set forth in claim 14 including means for cocking said actuating means.

16. A method for automatically discharging from an inhaler having a body, a nozzle and a valve responsive to relative displacement between the body and the nozzle a charge of medicated vapor into a user's oral cavity on initiation of inhalation by the user, said method comprising the steps of:
   (a) retaining the nozzle of the inhaler in a fixed location and slidably supporting the body of the inhaler in a housing;
   (b) actuating with an actuating mechanism disposed in an enclosure in fluid communication with the housing the valve of the inhaler to eject a charge of the medicated vapor by slidably repositioning the body of the inhaler toward the nozzle of the inhaler;
   (c) channeling the charge of medicated vapor through a conduit extending from the housing and having an outlet port and into the user's oral cavity upon insertion of the outlet port into the user's mouth;
   (d) triggering the actuating mechanism;
   (e) initiating operation of said triggering step in response to a pressure drop within the enclosure due to inhalation by the user, said initiating step including the steps of operating a trigger valve in response to the pressure drop to effect said triggering step;

(f) cocking the actuating mechanism prior to performance of said step of actuating; and (g) discouraging a flow of ambient air into the enclosure and from within the enclosure upon and with the flow of the discharged medicated vapor;

whereby, on placement of the outlet port within the user's mouth and upon inhalation of the user, a pressure drop within the enclosure occurs to trigger the cocked actuating mechanism and bring about a discharge and channeling of medicated vapor from the inhaler into the user's oral cavity and lungs.

17. The method as set forth in claim 16 wherein said initiating step includes the step of sensing inhalation by the user.

18. The method as set forth in claim 17 wherein said triggering step includes the step of uncocking a mechanism for effecting said actuating step.

19. The method as set forth in claim 18 wherein said actuating step includes the step of biasing the body of the inhaler toward the nozzle of the inhaler subsequent to said uncocking step.

* * * * *